(12) United States Patent
Webster et al.

(10) Patent No.: US 8,269,067 B2
(45) Date of Patent: *Sep. 18, 2012

(54) SLOW-MATURING, DETERMINATE PEAS

(75) Inventors: David Webster, Twin Falls, ID (US); Carl J. Braun, III, Woodland, CA (US)

(73) Assignee: Seminis Vegetable Seeds, Inc., St Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,702

(22) Filed: Dec. 20, 2010

(65) Prior Publication Data

US 2011/0088127 A1  Apr. 14, 2011

Related U.S. Application Data

(63) Continuation of application No. 11/908,263, filed as application No. PCT/US2006/008618 on Mar. 10, 2006, now Pat. No. 7,906,708, which is a continuation of application No. 11/078,603, filed on Mar. 10, 2005, now abandoned, said application No. 11/908,263 is a continuation of application No. 11/078,603, filed on Mar. 10, 2005, now abandoned.

(60) Provisional application No. 60/714,525, filed on Mar. 18, 2005.

(51) Int. Cl.
*A01H 5/00* (2006.01)
*A01H 5/10* (2006.01)

(52) U.S. Cl. ...................................... 800/298
(58) Field of Classification Search ............... None
See application file for complete search history.

(56) References Cited

U.S. PATENT DOCUMENTS

| | | | | |
|---|---|---|---|---|
| 5,523,520 | A * | 6/1996 | Hunsperger et al. | 800/260 |
| 7,906,708 | B2 * | 3/2011 | Webster et al. | 800/298 |
| 2006/0206968 | A1 | 9/2006 | Webster et al. | |
| 2008/0301843 | A1 | 12/2008 | Webster et al. | |
| 2010/0017903 | A1 | 1/2010 | Webster et al. | |

FOREIGN PATENT DOCUMENTS

WO    WO 2006/099152 A2    9/2006

OTHER PUBLICATIONS

Kraft et al (2000, Theor. Appl. Genet. 101:323-326).*
Eshed et al (1996, Genetics 143:1807-1817).*
Davis et al (1995, HortScience 30(3):639-640).*
Asgrow Seed Company, Plant Variety Protection Certificate No. 7100039 (1973), provided in U.S. Appl. No. 11/078,603.
W. Brotherton Seed Co., Inc., Plant Variety Protection Certificate No. 7100020 (1974), provided in U.S. Appl. No. 11/078,603.
Cousin, "Peas (*Pisum sativum* L.)," *Field Crops Research*, 53(1-3):111-130 (1997), provided in U.S. Appl. No. 11/908,263.
Ellis et al., "An Integrated and Comparative View of Pea Genetic and Cytogenetic Maps," *New Phytologist*, 153:17-25 (2002), provided in U.S. Appl. No. 11/908,263.
Foucher et al., "Determinate and Late Flowering are Two Terminal Flower1/Centroradialis Homologs that Control Two Distinct Phases of Flowering Initiation and Development in Pea," *The Plant Cell*, 15:2742-2754 (2003), provided in U.S. Appl. No. 11/908,263.
Hedley et al., "An Analysis of Seed Development in *Pisum sativum* II. The Effect of the *r*-Locus on the Growth and Development of the Seed," *Annals of Botany*, 58:371-379 (1986), provided in U.S. Appl. No. 11/078,603.
Hedley et al., "An Analysis of Seed Development in *Pisum sativum* XVII. The Effect of the *rb* Locus Alone and in Combination with *r* on the Growth and Development of the Seed," *Annals of Botany*, 74:365-371 (1994), provided in U.S. Appl. No. 11/078,603.
International Search Report, International Appln. No. PCT/US2006/08618 (Oct. 16, 2007), provided in U.S. Appl. No. 11/078,603.
International Preliminary Report on Patentability, International Application No. PCT/US2006/008618 (issued Dec. 6, 2007), provided in U.S. Appl. No. 11/908,263.
Lee et al., "An RFLP Marker for $r_b$ in Pea," *Theor. Appl. Genet.*, 75:362-365 (1988), herewith.
Lloyd et al., "Determination of the Effect of *r* and *rb* Mutations on the Structure of Amylose and Amylopectin in Pea (*Pisum sativum* L.)," *Carbohydrate Polymers*, 29(1):45-49 (1996), herewith.
Makasheva et al., "Determinate Growth Habit (*det*) in Peas: Isolation, Symbolization, and Linkage," *PNL*, 19:31-32 (1987), provided in U.S. Appl. No. 11/908,263.
Matta et al., "Inheritance and Mapping of Storage Protein Genes in *Pisum sativum* L.," *Heredity*, 48(3):383-392 (1982), provided in U.S. Appl. No. 11/908,263.
Murfet, "Interaction of the *det* (Determinate) Mutant with Other Flowering Genes," *PNL*, 21:44-47 (1989), provided in U.S. Appl. No. 11/908,263.
Murfet, "Flowering Genes in Pea and Their Use in Breeding," *PNL*, 22:78-86 (1990), provided in U.S. Appl. No. 11/908,263.
Ratnayake et al., "Pea Starch: Composition, Structure and Properties—A Review," *Starch*, 54(6):217-234 (Jun. 2002), provided in U.S. Appl. No. 11/908,263.
Supplementary European Search Report, European Application EP 06 73 7763 (completed Sep. 24, 2009), provided in U.S. Appl. No. 11/908,263.
Swiecicki, "Determinate Growth (det) in *Pisum*; A New Mutant Gene on Chromosome 7," *PNL*, 19:721-73 (1987), provided in U.S. Appl. No. 11/908,263.
Swiecicki et al., "Localization of Important Traits: The Example Pea (*Pisum sativum* L.)," *Biotechnology in Agriculture and Forestry*, vol. 53 (eds. H. Lorz and G. Wenzel), pp. 155-169, Springer Verlag, Berlin German (Jan. 2005), provided in U.S. Appl. No. 11/908,263.
"Cymose inflorescence," Definition at http://botanydictionary.org/cymose-inflorescence.html, Dictionary of Botany (2003), herewith.
Non-final Office Action, U.S. Appl. No. 12/565,445 (published as US 2010/0017903 A1) (Aug. 4, 2011), herewith.
"Racemose inflorescence" Definition at http://botanydictionary.org/racemose-inflorescence.html, Dictionary of Botany (2003), herewith.

* cited by examiner

*Primary Examiner* — Stuart F. Baum
(74) *Attorney, Agent, or Firm* — Alissa M. Eagle; Arnold & Porter LLP (57) ABSTRACT

A determinate pea plant, where peas of the pea plant have a wrinkled-seed phenotype, and where the pea plant is slow-maturing.

13 Claims, 2 Drawing Sheets

```
                  M   A   S   G   C   V   S   L   K   T   N   T   H   F   P   N   S   K   K   G   S
Rb: AACTCAAAAAAGCTTAGTTTTTTGAGGTTACTACAATGGCTTCTGGTTGTGTGAGCTTGAAACCAACACCCATTTCCAAATTCTAAAAAGGTTCTT
rb: AACTCAAAAAAGCTTAGTTTTTTGAGGTTACTACAATGGCTTCTGGTTGTGTGAGCTTGAAACCAACACCCATTTCCAAATTCTAAAAAGGTTCTT

F   F   G   E   R   I   K   G   S   L   K   N   S   S   W   V   T   T   Q   K   K   I   K   P   A   S   F   S   A   I   L   T   S   D
Rb: TTTTGGGGAAAGAATCAAAGGAAGCTTGAAACAGTTCATGGGTCACTACCCAGAAGAAGATCAAACCTGCTTCTTTTTCTGCTATTCTTACTTCAGA
rb: TTTTGGGGAAAGAATCAAAGGAAGCTTGAAACAGTTCATGGGTCACTACCCAGAAGAAGATCAAACCTGCTTCTTTTTCTGCTATTCTTACTTCAGA

D   P   K   G   S   L
Rb: TGACCCCAAAGGTTCCCTggtaaactcagtttttcattctgggtttccacttttgcttccaattctgaaaaaaagaagaaagactttttttctcccattatat
rb: TGACCCCAAAGGTTCCCTggtaaactcagtttttcattctgggtttccacttttgcttccaattctgaaaaaaagaagaaagactttttttctcccattatat N   L
Rb: gacataacttttttatgttaattatttgctacacatttttgtttttggtatatgatattgatttgagtgtatgtttgaaattcaGAATTT
rb: gacataacttttttatgttaattatttgctacacatttttgtttttggtatatgatattgatttgagtgtatgtttgaaattcaGAATTT SEQ ID 1: 5' AGGGCCTGGAACACATCTATC 3'
    Q   V   P   S   F   L   R   L   R   A   D   P   K   N   V   I   S   I   V   K   G   G   G   P   G   T   H   L   Y   P   L   T   K
Rb: GCAAGTGCCTTCATTCTGAGACTAAGAGCTGATCCAAAAAATGTGATTTCCATTGTGTTGGGAGGAGGGCCTGAACACATCTCTATCCTCTTACCAAA
rb: GCAAGTGCCTTCATTCTGAGACTAAGAGCTGATCCAAAAAATGTGATTTCCATTGTGTTGGGAGGAGGGCCTGAACACATCTCTATCCTCTTACCAAA R   A   A   T   P   A   V
Rb: CGAGCTGCAACACCTGCGGTTgagtgagttgagtgagttttatgatgagtttttatgatgatgattgtgtctgaattctaacatttggtgttgttgtaacttttgttgtctgtggtgatga
rb: CGAGCTGC---------GGTTgagtgagttttatgatgatgattgtgtctgaattctaacatttggtgttgttaacttttgttgtctgtggtgatga
                    3' CTCACTCAAAATACTACTTAACAAC 5' SEQ ID #2

P   V   G   G   C   Y   R   L   I   D   I   P   M   S   N   C   I   N   S   G   I   N   K
Rb: agatttgttgctgtgttgttttgaaggtCCTGTTGGAGGATGCTATAGGCTTATAGACATTCCAATGAGCAACTGCATCAATAGTGGCATCAACAAGA
rb: agatttgttgctgtgttgttttgaaggtCCTGTTGGAGGATGCTATAGGCTTATAGACATTCCAATGAGCAACTGCATCAATAGTGGCATCAACAAGA
```

Figure 1

Figure 2

SLOW-MATURING, DETERMINATE PEAS

CROSS-REFERENCE TO RELATED CASES

The present application is a continuation of U.S. patent application Ser. No. 11/908,263, filed Jul. 3, 2008, now U.S. Pat. No. 7,906,308, issued Mar. 15, 2011, which is a national phase application under 35 U.S.C. §371 of International Application No. PCT/US2006/008618, filed Mar. 10, 2006, which is a continuation of U.S. patent application Ser. No. 11/078,603, filed Mar. 10, 2005 (abandoned), and which also claims the benefit under 35 U.S.C. §119 of U.S. Provisional Application No. 60/714,525, filed Mar. 18, 2005; U.S. patent application Ser. No. 11/908,263 is also a continuation of U.S. application Ser. No. 11/078,603, filed Mar. 10, 2005 (abandoned); each of which are herein incorporated by reference in their entireties.

INCORPORATION OF SEQUENCE LISTING

The file named "P30662USO4_seqlist.txt," which is 5,724 bytes in size (measured in Windows XP) and which was created on Dec. 20, 2010 is herein expressly incorporated by reference.

BACKGROUND OF THE INVENTION

1. Field of the Invention

The present invention relates to slow-maturing, determinate pea plants with improved growth and processing traits.

2. Description of Related Art

The garden pea (*Pisum sativum* L.) is an important crop plant, with many uses. Seeds of the pea plant, or peas, are consumed in either a dry mature form or in an immature state. The dry mature seed is used for human consumption and as animal feed. Seeds harvested in their immature form are commonly referred to as fresh peas, or garden peas, and are used as fresh vegetables or processed, typically by canning or freezing.

Peas have also proven to be useful experimental plants. Peas are normally self-pollinating, as the carpels and stamens are enclosed within the petals of the plant's flowers, and are therefore naturally pure breeding. In the 1860s, Gregor Mendel discovered the basic rules of inheritance by making various pea crosses and examining the phenotypic ratios of F2 progeny. Among other things, Mendel identified a locus called rugosus that is expressed, as a recessive trait, as a wrinkled appearance of the seed; presence of the dominant allele, R, leads to round seeds. This locus was later re-named r (White, *Proc. Am. Phil. Soc.* 56, 487-588 (1917)). Bhattacharyya et al. ((1990) Cell 60:115-122) demonstrated that the r locus encodes for a starch branching enzyme.

Simple sugars, such as fructose, glucose and sucrose, are sweet tasting to humans, while more complex carbohydrates, like starch, are not. Biochemical conversion of simple sugars to starch occurs in plants in both the cytosol and in the plastid, via 10-12 enzymatic steps. Any mutant that slows the conversion of sugars to starch can result in a phenotype of sweeter tasting immature peas and wrinkled seed.

Of particular note is the rb locus, which encodes the large subunit of the adenosine disphosphate glucose pyrophosphorylase gene, abbreviated ADPGPP. The ADPGPP enzyme is a heterotetramer in plants, with two small and two large subunit components. The rb mutant, when present as a homozygote (rb/rb) causes a decreased enzyme activity and slows starch accumulation. The rb mutant is also known as the alsweet gene, due to its effect on taste.

Peas with recessive genotypes at the r and rb loci (r/r and rb/rb) produce seeds that are typically sweeter than peas with only one recessive mutation (r/r or rb/rb).

In addition to the r and rb loci, researchers have found a number of other mutants in the starch synthesis pathway. Five wrinkled-seed loci that affect the starch content of the seed are r and rb, plus rug3, rug4 and rug5. The locus named low amylose (lam) influences starch, but not seed shape. The positions of these mutations in the pathway have been described (Wang et al. (1998) *J. Exp Bot* 49:481-502). rug3, rug4, rug5 and lam correlate to various mutations in genes for phosphoglucomutase, sucrose synthase, starch synthase for amylase and starch synthase for amylopectin, respectively. All of these mutants decrease the starch content of the seed to varying degrees by adversely affecting the activity of enzymes in the biosynthetic pathway through which sugars are converted to starch, thereby leading to sweeter peas. (Hedley, C. L., et al. (2002) *Starch/Stärke* 54: 235-42).

Determinate and indeterminate growth habits are available in peas, differing in whether or not the plants set a terminal flowering node. As only the first two or three reproductive nodes of indeterminate peas actually contribute to yield of fresh peas, pods set at the fourth node or higher do not contribute to the crop, and are generally discarded as waste.

In contrast, determinate peas set a terminal flowering node, with two racemes of pods, at the second or third reproductive node. Compared to indeterminate varieties, which set pods at nodes that do not contribute to yield, determinate varieties are expected to have a higher yield potential, from the elimination of wasted resources, and could be expected to produce more uniform peas. Determinate varieties should also be easier to harvest than indeterminate varieties because they stand more upright and bear pods at the top of the plant.

One drawback to developing determinate varieties for fresh pea production has been the perception that such peas mature more rapidly than indeterminate types, and that the harvest window of the immature and still sweet peas would be very short, i.e., the varieties are "flashy". Flashiness, or rapid maturity, tends to create difficulties for growers, especially where weather conditions or simultaneous maturity of multiple fields may prevent harvesting during the relatively narrow available window. This perception has limited the use of the determinate trait by pea breeders; for instance, no one has developed a commercial determinate variety with dark green immature peas.

Another drawback to determinate peas is that the original source of determinacy (det) in peas is tightly linked to the dominant Pa allele, which results in immature seeds that are light green. Consumers strongly prefer dark green peas, making a determinate light green variety virtually unmarketable under present conditions. The Pa and det loci are tightly linked on linkage group V. In order to develop determinate dark green peas that would be suitable for processing and the market, the close linkage between Pa and det must be broken, and a pa det/pa det genotypic combination created through a recombinational event. This event is rare between loci so tightly linked.

There remains a need, then, for fresh processing pea plants having high consumer acceptance for color and sweetness, and good horticultural characteristics such as the ease of harvest provided by determinate peas, but with a maturity rate permitting a harvest window comparable to that of indeterminate commercial pea plants.

SUMMARY OF THE INVENTION

The present invention provides a determinate pea possessing good horticultural traits adapted for commercial pea production, including delayed maturity (see definition as follows). A novel method is provided to produce not only determinate pea plants with the desired slow-maturing phenotype but pea plants with a novel genotype in the development of sweetness. Therefore, the present invention relates to (i) determinate slow-maturing pea plants, (ii) methods for producing such plants.

In one embodiment, determinate wrinkled-seed pea plants are provided that mature substantially slower than (i) other determinate pea plants, including other determinate pea plants with dark green seeds and (ii) at least some known commercial pea plants, such as the variety Estancia (Seminis, Inc., Oxnard, Calif.). Thus, slow-maturing pea plants are provided that accumulate starch at a rate of about 90% or less, more preferably about 75% or less, even more preferably about 67% or less, and most preferably about 50% or less than the starch accumulation rate of Estancia, when grown in similar field conditions. Estancia is a well-known and widely distributed commercial pea variety, as well as a protected variety described in PVPA Certificate No. 9900272. For purposes of evaluating maturity rates samples of Estancia may be obtained through normal commercial channels, or may be obtained directly from Seminis, Inc., upon request.

In reference to the deposited determinate pea line designated 085 2 0698, slow-maturing pea plants are provided that accumulate starch at a rate of about 180% or less, more preferably about 150% or less, even more preferably about 133% or less, and most preferably about equal to or less than the starch accumulation rate of line 085 2 0698, when grown in similar field conditions. Seed of inbred pea plant line 085 2 0698 was the subject of a patent deposit under the Budapest Treaty, as Accession No. ATCC PTA-6628, made on Mar. 11, 2005.

Pea plants of line 085 2 0698, as well as seed, pollen, ovule and other vegetative tissue derived from line 085 2 0698, or a pea plant regenerated from such tissue are also provided by this invention. Also contemplated is a pea plant having the physiological and morphological traits of the pea plant produced from the deposited seed.

In one aspect of the invention the pea plants have a double wrinkled-seed phenotype, though a variety of combinations of wrinkled seed traits may be used in combination, or in combinations with other traits known to affect the conversion of sucrose to starch. In a further aspect of this embodiment, a double wrinkled phenotype is conferred by the following combination of recessive alleles for wrinkled seeds: r/r and rb/rb.

In another aspect of this embodiment, the determinate growth phenotype corresponds to a homozygous det/det genotype.

In yet another aspect of this embodiment, a dark green pea phenotype is provided, for instance the dark green phenotype that corresponds to a homozygous pa/pa genotype.

In another embodiment, this invention provides dark green determinate pea plants with a double wrinkled phenotype from a combination of the following genotypes: det r/det r; det r/det r, rb/rb; and pa det r/pa det r, rb/rb.

A plurality of such pea plants may be grown in a field. A field of a plurality of pea plants in which substantially all of the pea plants are slow-maturing is also contemplated.

Also provided are pea pods and peas harvested from the pea plants of this invention. Also contemplated is a method for growing a plurality of pea plants of the present invention and harvesting pea pods of such plants. Such pea pods may be harvested through mechanical means.

In another aspect of the invention, a method is provided for breeding pea plants by making various crosses between pea plants with desired traits and genotypes and selecting for pea plants having the traits described above. One such method comprises the steps of (a) crossing a pea plant having a first wrinkled-seed phenotype with a pea plant having the rb wrinkled-seed phenotype, and (b) using a marker for the rb allele to screen pea plants of subsequent generations of the cross in (a) for the presence of the rb allele; where the marker has the characteristic of being identifiable using SEQ ID No.: 1 and SEQ ID. NO.: 2. Where the first wrinkled-seed phenotype is r, the method further comprises the step of (c) screening for the r allele by analyzing starch grain appearance Use of pea plants of the invention, such as for breeding purposes, is also provided by the invention.

These and other features and advantages of this invention are described in, or are apparent from, the following detailed description of various exemplary embodiments of the devices and methods according to this invention.

BRIEF DESCRIPTION OF THE DRAWINGS

Various exemplary embodiments of this invention will be described in detail, with reference to the following figures, wherein.

DETAILED DESCRIPTION OF THE PREFERRED EMBODIMENTS

Pea plants of the present invention are a variety of *Pisum sativum* L. with improved traits for harvesting and processing and/or a unique genotype. Specifically, slow-maturing determinate pea plants with dark green peas are provided having a double wrinkled-seed phenotype, such as is presented from the genotype r/r, rb/rb. This invention also relates to the discovery of peas with a novel genotype, pa det r/pa det r, rb/rb, and to methods for obtaining this genotype using a molecular marker assay for the rb locus.

DEFINITIONS

Seeds and Peas

"Pea" or "peas", as used herein, means the immature seeds of the pea plant, that are harvested for processing by canning or freezing, typically at 40-60% moisture content, or, for good quality peas, from about 90 to about 110 tenderometer, as measured by the FTC Model TU Tenderometer.

"Seed" or "seeds", as used herein, refers to mature seeds of the pea plant, or the end product of the reproductive process and the embryo of the next generation, typically harvested at 8 to 14% moisture content.

Tenderometer

"Tenderometer" is a measure of the force required to crush approximately 200 grams of peas, and has become a standard measure of quality for peas. Higher tenderometer values indicate a more advanced maturity of the peas; as more sugar is converted to starch the pea becomes firmer. Good quality processed green peas are typically harvested at tenderometer values of from about 90 to about 110.

"Tenderometer" is also the name given to the instrument for measuring and grading pea quality. The FTC Model TU is the most widely used Tenderometer (Food Technology Corporation, 45921 Marks Road, Suite 120, Sterling, Va. 20166, USA).

Alcohol Insoluble Solids

Alcohol insoluble solids (AIS) measures starch content, with higher AIS equating to higher starch, lower sugars, and lower consumer quality. In determining AIS, subsamples of specific plots at every harvest are canned and analyzed, and the level of AIS is measured, as more fully described below.

Heat Units and Starch Accumulation

Heat units are a measure of time corrected for the environmental effect of temperature. The base temperature for growth of peas is 40 F. Temperatures above 80 F do not mature peas at a more rapid rate than 80 F. Therefore an accumulation of heat units for a given day is computed by subtracting 40 from the average of the high and low temperatures for that day. A high temperature above 80 is recorded as 80 for the purpose of determining the average for that day. Heat units begin to accumulate at planting and are summed through all the days up to harvest. AIS values can be plotted against the corresponding HU at each harvest of a given variety. The slope of the resulting line provides the rate at which peas accumulate starch, as a measurement of AIS per heat unit value. A more level slope corresponds to a slower starch accumulation rate, whereas a higher slope reveals a rapid starch accumulation rate in response to HU.

By "starch accumulation rate", or "rate of starch accumulation", is meant, then, the slope of AIS values plotted against the corresponding HU, or the slope of AIS/HU, for a given variety. Pea lines show near linear starch accumulation rates. Least square linear regressions (Chatterjee et al. (2000) Regression Analysis by Example, $3^{rd}$ edition, Wiley, New York), provide a slope of the regressions for each line, which are an estimation of the starch accumulation rate. $R^2$ values are an indication of how well the data fit a linear model. The closer the $R^2$ values are to 1.0, the better the data fit a linear equation.

Loci and Alleles, Designations

While several systems have been devised to designate genotypes, as used herein genes segregating independently are shown unattached, with the loci separated by a comma (Suzuki, et al. (1981) An Introduction to Genetic Analysis, second edition, W. H. Freeman and Co., San Francisco). Because peas are diploids, there are alleles on each of two homologous chromosomes. Genotypes are abbreviated with the two allelic designations separated with a slash, such as Rb/rb. Genotypes at multiple loci are separated with a comma to indicate that the alleles segregate independently at these loci, e.g. r/r, Rb/rb. According to Ellis and Poyser (2001) New Phytologist (2002) 153: 17-25, the pa, det and r loci are all closely aligned on linkage group V. Weeden et al. showed that linkage group V is located on chromosome 3 (Weeden, N. F., T. H. N. Ellis, G. M. Timmerman-Vaughan, W. K. Swiecicki, S. M. Rozov, and V. A. Berdnikov (1998) Pisum Genetics 30:1-4). When loci are linked, genotypes are written to indicate the in cis, or in trans configuration of the alleles. For example, the abbreviation pa det r/Pa Det R indicates that the plant is heterozygous at these three linked loci, and the recessive and dominant alleles are each present in the in cis configuration.

Alleles at the Rb locus segregate independently of these traits. The original determinate line used in this experiment (obtained from Gerald Marx) is designated:

Pa det r/Pa det r, Rb/Rb.

Genotypes and Phenotypes

Starch grains of r varieties are fractured with the grains showing something of the appearance of a cut up pizza pie under magnification. r, rb varieties, and r, Rb varieties are similar in appearance.

Dark green processor varieties, like Estancia, are generally indeterminate and practically all have had the r allele for wrinkled seed. The genotype for Estancia is pa Det r/pa Det r, Rb/Rb.

Light green varieties, at one time used exclusively by processors for canning, were all indeterminate. Recently, however, light green varieties have become commercially unacceptable for fresh pea production in North America because of the consumer preference for dark green varieties. Obsolete light green varieties were once available with several starch mutants. In some parts of the world small sieve light green peas are still canned, while light green smooth peas are still used widely for animal feed (dry seed harvest).

Alsweet Peas were a spontaneous wrinkled-seed mutation from a type of pea called Alaska peas, now nearly obsolete, and certain varieties used in Europe having smooth seed and the Pa Det R/Pa Det R, Rb Rb genotype. The new mutation, designated rb, is called the "alsweet" gene. Alsweet varieties have the Pa Det R/Pa Det R, rb/rb genotype.

All other light green varieties have fractured starch grains due to the recessive allele at the r locus: Pa Det r/Pa Det r, Rb/Rb. Starch grains of double wrinkled R, rb lines are smooth, like those of smooth-seeded varieties.

Line 08520647 is a single wrinkled determinate pea with dark green immature seeds, and has fractured starch grains due to the recessive r trait: pa det r/pa det r, Rb/Rb.

Lines 085 2 0698 and 08540794 are double wrinkled-seed, determinate peas, with dark green immature seeds, (pa det r/pa det r, rb/rb). These lines also have fractured starch grains, due to the recessive r.

Characteristics of Slow-Maturing Peas

In one embodiment, slow-maturing pea plants of the present invention have a determinate growth habit, and wrinkled mature seeds. In another embodiment, the pea plants have a double wrinkled phenotype attributable to the genotype r/r, rb/rb. Each of these traits is described in detail below. The pea plants are preferentially dark green (pa/pa).

Determinate Growth Habit

Peas of the present invention have a determinate growth habit. Commercial pea growers often use the term determinate to refer to bush or dwarf peas with short internodes and concentrated pod set. Herein, the botanical definition of determinate is used to refer to a growth habit in which reproductive growth stops with an inflorescence at a terminal bud. Conventional peas used for processing are all indeterminate. Indeterminate peas do not produce a terminal node, but continue producing flowers and pods, such that the pods set at the fourth reproductive node or higher are discarded as waste during harvest.

The determinate pea plants of this invention set pods at only a few flowering nodes. Typically, pods are set at the first, second and possibly the third flowering node. Either the second or third flowering node will be the terminal node. Location of the terminal flowering node at the second or third reproductive node in a determinate variety is determined by genetic background effects and is expressed in a stable manner.

In one preferred embodiment, the determinate pea plants stand substantially upright. In another aspect of this embodiment, pods occur substantially at the top of the plant, which further contributes to ease of harvesting. The upright habit also provides more even exposure to sunlight, resulting in more uniform color of the immature peas from the increase in penetrating sunlight.

Due to reduced apical dominance, determinate pea plants often develop lateral branches that bear pods that mature later than pods at the top of the plant and thus do not contribute to yield of fresh peas, a tendency which is typically selected against in the process of breeding determinate varieties.

The determinate phenotype can only be observed when the two mutant det alleles are found in the homozygous condition. This fixed allelic combination is abbreviated as det/det. The det locus is located in linkage group V.

Immature Seed Color

Pea plants of the present invention may produce light green or dark green peas. In the preferred embodiment the peas are dark green, or the "dark green phenotype". The dark green phenotype is a recessive condition derived from the pa/pa genotype.

The allele for light green color, Pa, is tightly linked to the allele for determinacy, det. Because consumers prefer dark green peas, this linkage was bred against to obtain a dark green determinate phenotype. The resulting genotype is pa det/pa det.

Wrinkled-Seed Phenotype

Pea plants of the present invention preferably have wrinkled mature seeds, which is a trait associated with sweetness. This phenotype is referred to herein as "wrinkled", or "wrinkled-seed". The wrinkled phenotype may be caused by several different alleles, including r, rb and rug3.

In addition to the r and rb loci, researchers have found a number of other mutants in the starch synthesis pathway. In plastids, the first step in starch synthesis is the conversion of glucose-6-phosphate to glucose-1-phosphate; this step is catalyzed by a phosphoglucomutase. Mutations in the DNA sequence that codes for this enzyme are at the rug3 locus. Glucose-1-phosphate is then converted to adenosine diphosphate-glucose, by ADPGPP enzyme. The large subunit ADPGPP gene locus is designated rb, and the mutant allele is designated rb. ADPglucose molecules form starch by the enzymatic action of two different starch synthases; these loci are lam and rug5. Starch exists in varying ratios of the linear polysaccharide amylase and the highly branched polysaccharide amylopectin. Starch branching enzyme, whose gene inheritance was originally studied by Mendel, catalyzes the conversion of relatively linear glucose subunits to a more highly branched configuration; r is the designation for the mutant at this locus. An additional wrinkled-seed mutation at the rug4 locus relates to a defective sucrose synthase that acts in the cytosol of the plant cell.

Because these mutants are recessive, the wrinkled phenotype is only observed when the mutant alleles are found in the homozygous condition, such as r/r, or rb/rb. To varying degrees, these alleles all contribute to slowing production of starch. Double wrinkled peas are those that have at least two recessive homozygotes, such as r/r, rb/rb, contributing to the wrinkled phenotype.

In one embodiment, the double wrinkled phenotype is derived from the genotype r/r, rb/rb.

Rb is located at the top of chromosome 3 (Ellis et al. (1993) Pisum Newsletter 25:9). Pa, det and r are tightly linked in a separate linkage group (Ellis and Poyser (2001) New Phytologist).

A molecular marker test, as described below, is used to screen populations for the desired genotypes at the rb locus. The phenotype from a r/r, rb/rb genotype is not distinguishable visually from the phenotype from a r/r, Rb/_genotype. The r/r, rb/rb phenotype is also less competitive in the fruit (pod) and is preferentially aborted when it is present and segregating with the r/r, Rb/rb genotype; thus the distribution of segregants in the F2 generation is skewed away from the r/r, rb/rb phenotype. This effect is seen only when the phenotypes are segregating in the pod, as a matter of relative fitness. In homozygous and non-segregating pods, the r/r, rb/rb phenotype does not show a higher rate of abortion.

Wrinkled phenotypes derive from mutations that decrease the activity of various enzymes of the biosynthetic pathway used to convert simple sugars to starch. Peas having a wrinkled-seed phenotype are typically sweeter (i.e., retain more simple sugars) than peas with a smooth-seed phenotype. Peas having multiple wrinkled-seed phenotypes may be even sweeter than a single wrinkled-seed phenotype.

Peas of the present invention have good sweetness levels, compared to other known commercial varieties, as measured by sucrose and alcohol insoluble solid levels at tenderometer readings of about 90 to about 110. Preferably, peas of this invention contain from at least about 6.0 to at least about 7.5 percent sucrose by fresh weight, though the absolute numbers will vary considerably even within a line from location to location and season to season, due to environmental effects.

Similar Field Conditions

As used herein, "similar field conditions" refers to appropriate pea growing conditions for purposes of comparing lines, i.e., growth in the same field and season, in both a region and under conditions appropriate for growing peas.

Delayed-Maturity

Peas of this invention having the above-described traits are slow-maturing. The term "slow-maturing," "reduced maturity rate" or "delayed maturity" as used herein, refers to the rate at which pea plants accumulate starch in the immature seeds, or peas, as measured using the method described in Example 1. Briefly, pea plots of different varieties are harvested over several days. At each harvest, heat units, accumulated from the time of planting until harvest, and tenderometer values, are recorded for each plot.

The slow-maturing, determinate pea plants accumulate starch at a rate, in terms of AIS/HU, that is substantially slower than that for the commercial indeterminate wrinkled variety Estancia. This was unexpected for a determinate pea. Accumulation of starch, in AIS/HU, for a slow-maturing determinate pea will be at a rate that is at least about 90% or less than the rate of accumulation in Estancia, when grown in similar field conditions. In reference to the deposited determinate pea line, a slow-maturing pea accumulates starch, in AIS/HU, at a rate that is at least about 180% or less of the rate of accumulation in line 085 2 0698.

More preferred are slow-maturing peas having rates that are at least about 75% or less, more preferably at least about 67% or less, and most preferably about 50% or less than the rate of accumulation for Estancia, or, at least about 150% or less, more preferably at least about 133% or less, and most preferably about equal to or less than the rate of accumulation for line 085 2 0698, when grown in similar field conditions.

The slow-maturing, determinate pea plants preferably have a double wrinkled-seed phenotype, such as r/r, rb/rb. The pa det r/pa det r, rb/rb, pea plants described herein accumulate starch at a rate that is substantially slower than measured for line 085 2 0647, a determinate line with single wrinkled-seed phenotype and dark green peas. A multiple wrinkled phenotype may be a preferred mechanism for providing the slow-maturing trait to a determinate pea plant.

Plant Breeding

Plants having each parent line fixed for r were selected for an attempt to break the linkage between determinacy and light green pea color. Light green determinate pea plants (Pa det r/Pa det r, Rb/Rb) were crossed with dark green indeterminate pea (pa Det r/pa Det r, Rb/Rb). A crossing block was executed to break the tight linkage between the loci for determinacy and light green immature seed color. By "crossing block" it will be understood that a series of experiments were executed where an F1 was generated from a cross between the two homozygous parents, and desirable segregants were selected from the F2 or later generations.

More particularly, determinate light green pea plants were crossed with indeterminate pea plants having dark green seeds, with selection over several subsequent generations to find those segregants having determinate plant type and dark green pea color plants. A true determinate pea plant having dark green peas and wrinkled seeds from r/r was ultimately obtained from these experiments. This plant also had few lateral branches.

Dark green determinate plants having the r allele for the wrinkled trait and good horticultural characteristics (pa det r/pa det r, Rb/Rb) were then crossed with peas homozygous recessive for rb (Pa Det R/Pa Det R, rb/rb). Peas with two alleles for a wrinkled-seed trait are often sweeter than those that carry only a single wrinkled-seed allele.

The mutant phenotype from the r locus is determined relatively simply, by examining the appearance of the starch grains in the seed; fractured starch grains are characteristic for the phenotype caused by the r/r genotype.

Seeds with an rb/rb genotype are similarly wrinkled but have normal looking starch grains. In situations where another allele may already be providing the wrinkled trait, there is no visual starch trait that can be used to verify presence of the rb phenotype. With no visual check for the rb phenotype, obtaining a double wrinkled combination, say, r, rb, using conventional breeding techniques, such as test crosses, is laborious and time-consuming.

Additionally, when F2 generation hybrid pea plants encounter environmental stress, the double wrinkled seeds tend to be selectively aborted form the pods and do not form viable seeds. Thus, while 1 out of 16 seeds obtained from a self fertilization of an F1 hybrid parent having a R/r, /Rb/rb genotype would be expected to have the r/r, rb/rb genotype, that result actually occurs far less frequently. Likewise, while 1 out of 4 seeds obtained from an r/r, Rb/rb plant would be expected to carry the r/r, rb/rb genotype, the actual ratio is lower. From the need to conduct test crosses to identify plants with the rb/rb genotype and the tendency of plants to selectively abort r/r, rb/rb seeds, it is time-consuming and technically difficult to obtain plants with the double wrinkled phenotype.

To overcome this difficulty, a molecular marker was developed to determine the genotype at the rb locus. The rb locus encodes the large subunit of ADPGPP gene. Those skilled in the art recognize that there are several types of molecular tests that can be developed to discriminate the different allelic combinations at a locus. By no means limiting, then, a molecular marker test is described herein that discriminates the rb and Rb alleles by comparing the DNA at this locus. The sequence of the Rb allele (ADPGPP) mRNA product was published (Burgress, D. et al. (1997) Plant Mol. Biol. 33:431-444) and the sequence deposited into the National Center for Biotechnology Information (also referred to as Genbank) as accession number X96766. With the teachings of this disclosure, this DNA sequence can now be used to develop a molecular test to discriminate between the rb and Rb alleles.

Figure 1:
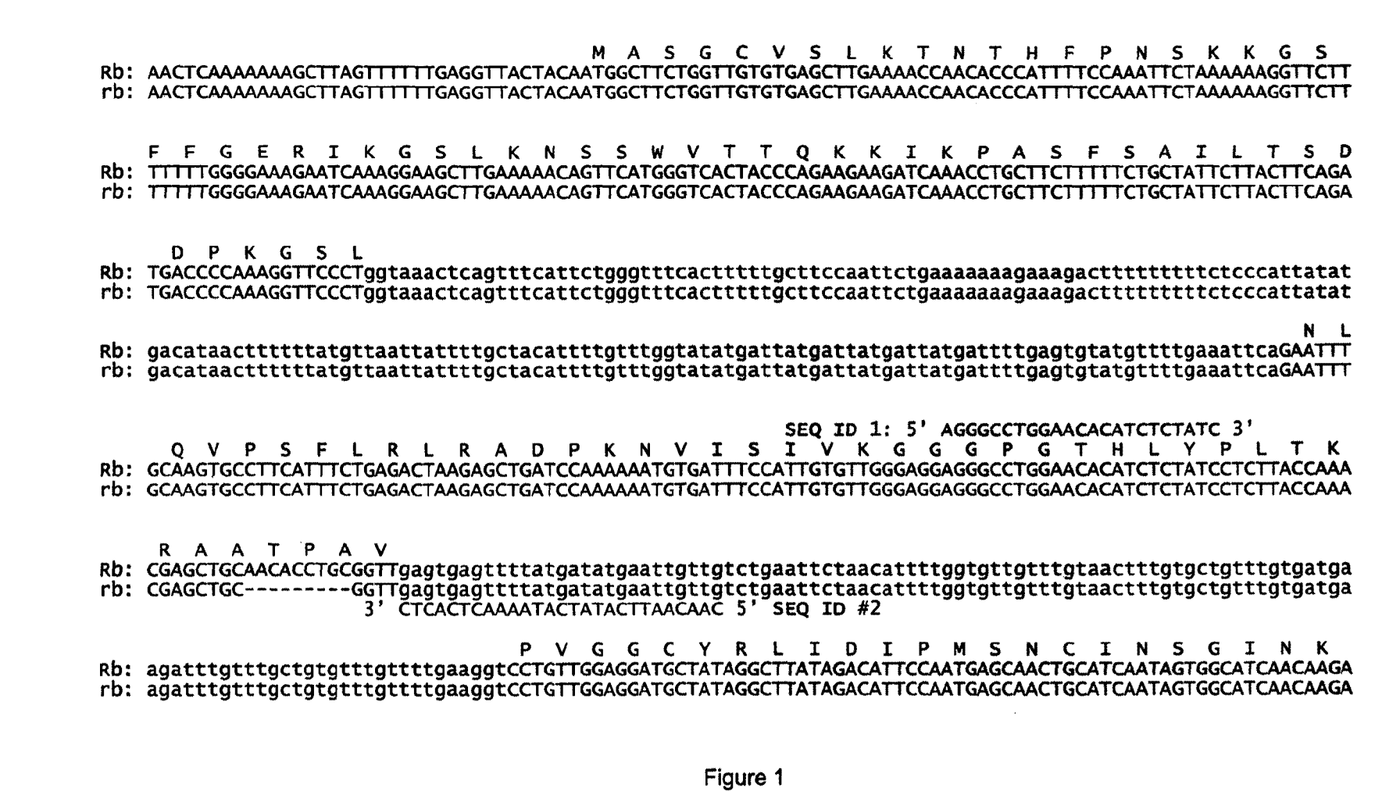
FIG. 1 shows a comparison of the DNA sequence in the region of the rb locus, in particular, the region comprising a 9 base pair (bp) deletion in the rb allele. The Rb sequence, spanning lines 2, 6, 10, 14, 19, 23, and 28, is disclosed as SEQ ID NO: 3. The protein sequence, spanning lines 1, 5, 9, 13, 18, 22, and 27, is disclosed as SEQ ID NO: 4. The rb sequence, spanning lines 3, 7, 11, 15, 20, 24, and 29, is disclosed as SEQ ID NO: 5.

Looking to FIG. 1, the recessive allele, rb, has a nine base pair deletion in its coding sequence, starting at base pair number 509, compared with the Rb allele. The 9 bp deletion results in 3 codons deleted. This small deletion in the rb allele leads to a reduction in the activity of the ADPGPP enzyme. In FIG. 1, the sequence in capital letters is the sequence from Genbank accession X96766, which is derived from cDNA. The deletion in the rb allele is shown with dashes.

The sequences in lower case are genomic DNA, which are not publicly available in any pea databank, and which were developed by additional sequencing from genomic DNA using techniques known to the art. The position of the two primers, SEQ ID NO: 1 and SEQ ID NO:2, are shown at the locations above and below where they will bind to the genomic DNA sequence. SEQ ID NO: 1 and SEQ ID NO: 2 thus provide the primer pairs that were synthesized and used for the marker assay:

SEQ ID NO: 1—agg gcc tgg aac aca tct cta tc
SEQ ID NO: 2—caa caa ttc ata tca taa aac tca ctc The region where SEQ ID NO: 2 is positioned is in the region of an intron. Initial experiments using only the cDNA information available from GENBANK produced a very large amplicon that included various intron sequences, far too large for discrimination among the Rb and rb alleles. Making a small PCR product was critical because it is more difficult to discriminate a 9 base pair difference as the fragments get larger.

The molecular assay disclosed herein uses a DNA amplification technique called the Polymerase Chain Reaction, or PCR. One advantage of PCR-based tests is that only very small samples of DNA are needed, and therefore, this often means that the tests are non-destructive. For the pea rb molecular test, only a small, approximately $0.5\ cm^2$ sample of leaf material is needed to perform the test. This small sample does not harm the plant in its development, such that the breeder can still use the plants for crossing or horticultural evaluations.

The marker method described provides an assay to discriminate between the Rb and rb alleles using a DNA-based test. Those skilled in the art will recognize that by using the information provided about the rb sequence in FIG. 1, other molecular assays can be designed to discriminate the Rb and rb alleles using standard molecular biology techniques. In other words, various suitable marker are identifiable using SEQ ID No.: 1 and SEQ ID. NO.: 2.

For instance, the DNA sequence of the PCR amplicon (81 bp) produced by these primers may provide a marker using various amplification and hybridization methods well-known to those of skill in the art. Further, probes have substantial identity to such marker DNA, preferably, having at least about 90% sequence identity, even more preferably at least about 95% sequence identity and most preferably at least about 98% sequence identity can be used to identify the rb allele and be similarly used to overcome the difficulties described above in obtaining plants with the r/rb combination.

Plants are then selected for the double wrinkled phenotype by analyzing starch grain appearance. In a preferred embodiment, the above methods may be used to obtain pea plants that are determinate, dark green, and double wrinkled, wherein the double wrinkled trait is attributable to the r/r, rb/rb genotype.

Characteristics of the Novel Lines of Pisum Sativum

As shown in Example 1, pea plants are provided that accumulate starch at a rate that is substantially slower than the rate at which determinate dark green pea plants accumulate starch. The rate actually compares very favorably to the rate at which the indeterminate, wrinkled-seed and dark green variety, Estancia, accumulates starch. Specifically, pea plants of the present invention accumulate starch at a rate of less than about 90% of the AIS/HU rate for Estancia, more preferably at a rate of less than about 75%, even more preferably at a rate of less than about 67%, and most preferably at a rate of less than about 50% of the AIS/HU rate for Estancia.

In terms of deposited determinate pea line 085 2 0698, pea plants of the present invention accumulate starch at a rate of less than about 180% of the AIS/HU rate, more preferably at a rate of less than about 150%, even more preferably at a rate of less than about 133%, and most preferably at a rate that is equal to or less than the AIS/HU rate for line 085 2 0698.

The low AIS/HU rates reflect a dramatic delay in maturity rates, something unexpected for determinate lines. This delay is advantageous to the grower in a number of ways. The peas are sweeter longer, providing a broader harvest window, which allows greater flexibility to the grower in determining the time of harvest, mitigating to some extent exigencies in weather and allowing greater ease of coordination with other operations. The peas will remain sweet on the vine during several days of delay, until weather or other conditions become favorable to harvest.

The determinate, double wrinkled phenotype lines described herein provide the first *Pisum sativum* lines available to the grower that combine the characteristics of determinate growth habit in a slow-maturing pea plant.

The trait of dark-green immature seeds in a slow-maturing, determinate line is a further benefit to the grower, as dark green is the current consumer preferred color for fresh or canned peas. The double-wrinkle phenotype is a further benefit, providing a sweet line for the consumer.

EXAMPLES

Example 1

Development Of Double Wrinkled, Determinate, Dark Green Lines

In an effort to focus on the segregation of the det and Pa alleles, determinate light green peas of line B387-426 were crossed with R87 223. B387-426, genotype Pa det r/Pa det r, Rb/Rb, is a germplasm release obtained in 1988 from the late Gerald A. Marx, of the Geneva Experiment Station of Cornell University. R87 223 is a productive mid-season, indeterminate dark green breeding line, genotype pa Det r/pa Det r, Rb/Rb.

Since the r and rb alleles are fixed in the F1 generation, this cross focused on the segregation of the Pa and det alleles, however, in the process of selection from this cross it was observed that the determinate characteristic consistently co-segregated with light green color; no recombinants having a determinate trait combined with dark green seed color were observed, confirming reports that the det and pa loci are tightly linked.

Many of the selections from this cross were also discarded due to an excessive numbers of lateral branches. Lateral branches typically develop in the absence of apical dominance, and determinate varieties are prone to this condition. Lateral branches bear pods that mature after those at the top of the plant and hence do not contribute to the yield of fresh peas, so this tendency must be selected against.

A selection from this cross, R93 398, was identified as having excellent productivity and few lateral branches. The genotype of R93 398 is Pa det r/Pa det r, Rb/Rb.

The next season a large crossing block was executed to break the linkage between the alleles for determinacy and light green color, Pa and det. The crosses involved R93 398 and several other dark green, indeterminate lines with the intention of breaking the linkage between Pa and det. One such line was R93 2085.01 (pa Det r/pa Det r, Rb/Rb).

F1 seeds from this series of crosses were grown and the plants selfed in the greenhouse. Approximately 3500 F2 seeds were planted in the field in the spring. From these 3500 plants 90 putative pa det/pa det selections were made (2.6%). The next year, 88 F3 lines from these selections were observed and it was determined that 13 of them (0.3%) actually recombined the det allele with the pa allele into lines of the genotype pa det r/pa det r, Rb/Rb.

One of the lines was designated R96 924.01. Through a process of self pollination and selection this line gave rise to R97 2609. R93 2085.01 was used as seed parent in the original cross pollination that led to R97 2609, with R93 398 as pollen parent. The genotype of R97 2609 is confirmed as pa det r/pa det r, Rb/Rb.

A new crossing block was executed in order to combine the recessive alleles for det, r, and pa with the recessive allele for Rb. Three of the pa det r/pa det r, Rb/Rb lines, namely, R97 2609, R97 2664, and R97 2678, were crossed to a pa Det r/pa Det r, rb/rb line, R97 2578. R97 2578 was indeterminate but carried both the r and rb alleles for wrinkled seed and had dark green immature peas.

Uniform stable pea lines with the pa det r/pa det r, rb/rb genotype were developed using self pollination and a combination of pedigree selection and single seed descent from the above crosses. The presence of r was verified by appearance of the starch grains, while rb was verified using the DNA marker described above.

Lines 085 2 0698 and 08540794 were both selected from the cross of R97 2609 as seed parent and R97 2578 as pollen parent. Both are genotype pa det r/pa det r, rb/rb. 085 2 0698 normally matures to 100 tenderometer at about 1430 heat units and has an average sieve size distribution, a measure of the size of the immature pea, of about 2.85 at 100 tenderometer. 08540794 matures at about 1480 heat units with an average sieve size distribution of 2.95. Both carry the afila foliage mutation in which leaflets are modified and borne as additional tendrils.

Example 2

Method for Identifying the rb Genotype Using the Marker Using a Molecular Marker Assay This method has two steps. The first step is to isolate DNA from the pea plant as the substrate for the molecular marker assay in the second step.

Isolation of Pea DNA for Marker Tests.

The following protocol can be used to extract pea DNA for subsequent molecular marker testing. Those skilled in the art will recognize that many DNA extraction protocols are available. All chemicals described in the protocol can be obtained from Sigma Chemical Company, Saint Louis, Mo. The procedure involves the following steps:

1. Collect a plant part that is approximately the size of a well in the 96 well microtiter plate format. Preferably, either a seed sample is used, or a tissue sample is taken from young leaves.

2. Add 150 µl extraction buffer (200 mM Tris-HCl, pH 7.5; 250 mM NaCl; 25 mM EDTA; 0.5% SDS) to the sample and macerate the tissue.

3. Centrifuge the plate for 15 minutes at 1900-x g at 15° C.

4. Transfer 100 µl of the supernatant fraction to a new 96 well plate that contains 100 µl of 2.5M potassium acetate (pH 6.5) in each well. Mix by shaking for approximately 2 minutes at 200 rpm.

5. Centrifuge the plate for 15 minutes at 1900-x g at 15° C.

6. Transfer 75 µl of the supernatant fraction to a new 96 well plate containing 75 µl isopropanol. Mix, then shake for 2 minutes at 200 rpm.

7. Centrifuge the plate for 15 minutes at 1900-x g at 15° C.

8. Remove supernatant fraction and add 200 µl 70% ethanol to the pellet fraction. Shake at 200 rpm for 5 minutes, and then incubate overnight at −20° C.

9. Centrifuge the plate for 15 minutes at 1900-x g at 15° C.

10. Remove supernatant fraction. Add 200 µl of 70% ethanol to the pellet, allowing the alcohol to wash the pellet for 1 hour at room temperature.

11. Centrifuge the plate for 15 minutes at 1900-x g at 15° C.

12. Discard the supernatant fraction and dry the pellet fraction at room temperature. This takes about 1 hour.

13. Dissolve the pellet fraction in 100 µl TE (10 mM Tris, pH 8.0, 1 mM EDTA, 5 µg/ml RNAase A) for 15 minutes at 37° C. Unless proceeding to the PCR step, the DNA can be stored at 4° C. or −20° C.

Molecular Marker Test

The design of PCR assays are well known to those skilled in the art. In the test disclosed herein, two single-stranded synthetic DNAs, called primers are designed to anneal to the rb locus, to each of the complementary DNA strands, such that the PCR amplicon that will be produced will contain the deleted region of the gene in the rb mutant allele. These primers are typically about 15 and 30 nucleotides in length (SEQ ID NO: 2 is 27 nucleotides); these stretches of nucleotides match the DNA sequence of the substrate at the marker locus to be amplified. Primers are designed such that they will facilitate the synthesis of an amplicon typically between 50 to 1,000 base pairs. Those skilled in the art know how to design these primers to create PCR-type assays, and often use software programs, like the publicly available Primer3 software (Whitehead Institute, Cambridge, Mass.) to assist in the design.

Primers can be synthesized using methodology known to the art, or purchased from any number of custom oligonucleotide companies. All primers used in these assays were purchased from the Operon Company, Alameda, Calif. Other reagents in the PCR reaction can be purchased from any number of commercial suppliers; in the assays described herein, the four deoxyribonucleotide-5' triphosphates (dNTPs) were purchased from the Pharmacia Company, Kalamazoo, Mich., and the PCR buffer and the Taq polymerase enzyme were purchased from the Applied Biosystems Company, Foster City, Calif. Those skilled in the art will also recognize that there is some flexibility in performing PCR assays as there are many types of PCR machines and assay conditions that can be used. A model 9700 PCR machine from the Applied Biosystems Company, Foster City, Calif., was used with the following run parameters.

An initial denaturation step for 2 minutes at 94° C. was followed by 35 cycles of amplification. Each amplification cycle had three steps of 30 seconds at 92° C., then 30 seconds at 50° C., then 30 seconds at 72° C. After the 35th cycle, the samples were held at 72° C. for 5 minutes. Although this ends the PCR amplification assay, the PCR machines were programmed to hold the finished reactions at 25° C. until retrieved by the researcher.

Those skilled in the art will recognize that there is considerable flexibility allowed in the PCR assay conditions. PCR reactions were prepared with 1 µL of the DNA template, 5.0 picomoles each of the two assay-specific PCR primers (SEQ ID 1 and SEQ ID 2), a final volume of 200 µM for each of the four dNTPs, 2.54 of 10×PCR buffer, and 1.25 units of Taq polymerase. Sterile water was used to bring the final volume of the reactions to 25 µL. These conditions produce amplicons of slightly different sizes that correlate with the presence of Rb and rb alleles. Specifically, a 81 base pair PCR amplicon is created when the Rb allele is present, and a 72 base pair amplicon is created when the rb allele is present. Both DNA fragments are synthesized when the plant is heterozygous (Rb/rb). These DNA fragments can be scored by electrophoretic resolution on either polyacrylamide or agarose gels. Not limiting, one may resolve these fragments on a 3.5% w/v Metaphor-type agarose gel (an agarose for resolving small fragments from Cambrex Bioscience Rocklin, Inc., Rocklin, Me.).

Example 3

Sucrose Analysis of Peas

Plots were harvested on multiple days, and at each harvest the accumulated heat units and tenderometer values were recorded. The accumulated heat unit for each plot at 100 tenderometer was calculated by linear regression.

Samples from the *Pisum sativum* varieties or lines are stored in cans until extracted. Peas are sub-sampled and weighed out on a Mettler AT200 analytical balance. Absolute ethanol is added to the sub-sample (4:1 ratio, volume/weight). The sample is cooled and stored overnight (at −20.degree. C.) then ground with an IKA Ultra Turrax T25 homogenizer. The homogenate is returned to the freezer. The following day, the sample is mixed, then centrifuged to clarify the extract. An aliquot is removed and scaled in an auto-sampler vial and sealed in an auto-sampler vial and stored at −20.degree. C. until analyzed.

The sugars are separated on a Hewlett-Packard 1050 HPLC chemstation system, employing a refractive index detector. The column used is a Whatman Partsil 5PAC column (4.times.12.5 mm). The solvent system is composed of 85% acetonitrile at a flow rate of 0.85 ml/minute at 35.degree. C. The injection volume is 5 microliters. A standard mixture of sucrose in 80% ethanol is used to quantify sucrose. This standard is injected every tenth sample.

Example 4

Alcohol Insoluble Solids Analysis

Lines of peas were canned and stored for up to one year. Alcohol insoluble solids content on canned peas from several different *Pisum sativum* lines. The protocol for determining the alcohol insoluble solids on these canned peas is as follows:

a) Open a can, pour the contents over an 8 mesh sieve, rinse with two volumes of tap water, and allowed to drain for two (2) minutes;

b) Weigh 90-100 grams of peas to the nearest 0.1 gram, transfer to a blender cup, add to the cup an equal volume of deionized water;

c) Blend the peas for two (2) minutes on the blend setting;

d) Weigh 40 grams of the blended mix to the nearest 0.01 grams and transfer quantitatively to a 1 liter boiling flask fitted with a reflux condenser. 280 ml of 86% ethanol is used to complete the transfer;

e) Boil the mixture for 30 minutes;

f) Place an 11 cm Whatman #1 filter paper, previously dried in a metal weighing dish and weighed to the nearest 0.01 grams, into an 8 cm Buchner filter apparatus, in a manner so that the edges of the paper extend 1 cm up the sides of the filter apparatus, and apply suction to the apparatus and filter the alcohol-solids mixture quantitatively through the paper; wash the residue from the flask with 80% ethanol until the washings are colorless (do not overfill the cup formed by the filter paper); and g) Return the filter paper to a drying oven in its original metal weighing dish and dry at 100 degree C. for 2 hours; cool in a desiccator and weigh to the nearest 0.01 grams; determine the weight of dry, alcohol insoluble solids by difference and multiply by 5 to convert to percentage alcohol insoluble solids.

The alcohol insoluble solids value for each of the lines at specific tenderometer is calculated using linear regression from paired measures of alcohol insoluble solids and tenderometer for each variety. The tenderometer value at 12% alcohol insoluble solids is calculated by linear regression from the same paired data.

Example 5

Analysis of AIS Levels

The field trial was conducted with the slow-maturing peas and control peas, including line 08520647, a single wrinkled determinate pea with dark green immature seeds, and Estancia, an indeterminate variety with no terminal flowering node and many reproductive nodes. Estancia also has the r/r genotype that results in wrinkled mature seed.

Subsamples from each harvest of each plot were canned and later analyzed for two measures each of alcohol insoluble solids (AIS), according to the methods described above. Three separate harvests of 08520647 (0647), four separate harvests of 08540794 (0794), and four separate harvests of Estancia were made in one trial. Table 1 provides the raw data for the HU measurements and AIS for this experiment.

TABLE 1

| Line | Date | HU | Tndr | % AIS |
| --- | --- | --- | --- | --- |
| 085 2 0647 | 6/24 | 1387 | 91 | 9.1 |
| 085 2 0647 | 6/24 | 1387 | 91 | 9.425 |
| 085 2 0647 | 6/25 | 1407 | 97 | 10.2 |
| 085 2 0647 | 6/25 | 1407 | 97 | 10.575 |
| 085 2 0647 | 6/26 | 1435 | 115 | 12.325 |
| 085 2 0647 | 6/26 | 1435 | 115 | 12.05 |
| Estancia | 6/27 | 1464 | 87 | 8.55 |
| Estancia | 6/27 | 1464 | 87 | 8.95 |
| Estancia | 6/28 | 1484 | 89 | 9.05 |
| Estancia | 6/28 | 1484 | 89 | 9.5 |
| Estancia | 6/29 | 1512 | 99 | 10.7 |
| Estancia | 6/29 | 1512 | 99 | 10.875 |
| Estancia | 6/30 | 1532 | 116 | 13 |
| Estancia | 6/30 | 1532 | 116 | 13.35 |
| 085 4 0794 | 6/29 | 1512 | 87 | 7.75 |
| 085 4 0794 | 6/29 | 1512 | 87 | 8.45 |
| 085 4 0794 | 6/30 | 1532 | 95 | 8.75 |
| 085 4 0794 | 6/30 | 1532 | 95 | 9.2 |
| 085 4 0794 | 7/1 | 1557 | 102 | 9.775 |
| 085 4 0794 | 7/1 | 1557 | 102 | 9.65 |
| 085 4 0794 | 7/2 | 1583 | 109 | 10.625 |
| 085 4 0794 | 7/2 | 1583 | 109 | 10.45 |

Figure 2:
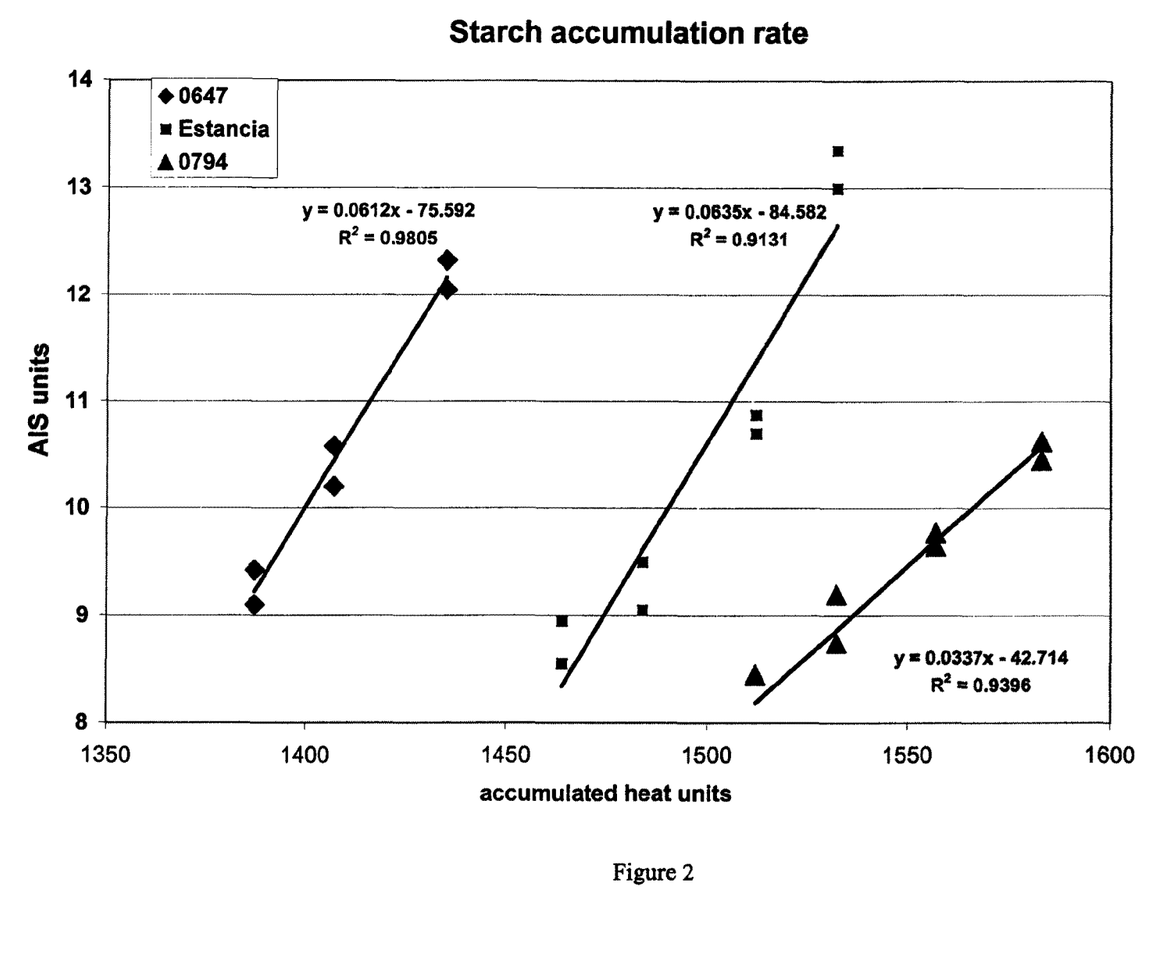
FIG. 2 is a graph with measurements of alcohol insoluble solids for various peas plotted against the corresponding heat unit value. The slope of the graph provides the rate at which starch accumulates in peas of the tested pea plants.

FIG. 2 is a graphical presentation of starch accumulation. The X axis measures accumulated heat units; higher heat units correlate with maturation. The Y axis measures alcohol insoluble solids, higher AIS values indicate higher starch accumulation. Starch accumulation rates, in terms of the slope of the data for each of the three lines are provided (0647, Estancia and 0794). All three lines in FIG. 2 show highly linear starch accumulation rates.

Lines 0647 and Estancia show similar slopes of 0.0612 and 0.0635, respectively. In contrast, line 0794 has a much reduced starch accumulation rate, with a slope of 0.0337. A dotted blue horizontal line at the AIS value of 12 indicates a generally acknowledged industry standard. Peas below this AIS value are considered Grade A products, while peas above this line are lower quality. An advantage of line 794 that is clearly observed from the data in FIG. 2 is that the line has a slow maturation rate, indicated by a lower slope value compared with the other lines. This slow maturation rate provides a longer harvest window, which is desired by growers. Additionally, line 794 consistently produces high quality peas, because of the reduced starch levels.

These results indicate that under standardized conditions, line 0794 accumulates starch, as a function of AIS/HU, at a rate only about half as fast as Estancia accumulates starch (53% of the Estancia rate), and only about half as fast as the determinate, dark green, single wrinkled line 0674. For lines 0647 and Estancia, determinate and indeterminate single r wrinkled-seed phenotype lines, respectively, accumulate starch at roughly the same rate. This is somewhat surprising due to the fact that 0647 is a determinate line, and might be expected to mature even faster than an indeterminate single r wrinkled-seed phenotype line. Other aspects of the genetic background may play a role, as well, explaining the similarity in starch accumulation rates for these particular determinate and indeterminate lines. In any case, from the comparison of 0647 and 0794, determinate and indeterminate lines, respectively, having similar genetic backgrounds, it appears that the single r wrinkled-seed phenotype is insufficient, of itself, for a slow-maturing determinate pea plant.

In a previous season, under different conditions, the slope of the line for Estancia was determined to be 0.0443 AIS/HU, while the slope of the line for the pa det r/pa det r, rb/rb line 085 2 0698 was 0.0225 AIS/HU, which demonstrates that line 085 2 0698 also accumulates starch at only about half the rate as does Estancia (51% of the Estancia rate).

Example 6

Creation of Inbreds and Hybrids

Using known methods, breeders may obtain inbred lines of the slow-maturing, determinate, double wrinkled peas of the present invention. Inbred lines having the slow-maturing and other traits of the present invention are described above. Seed from line 085 2 0698, described above, has been deposited with the American Type Culture Collection as Accession No. PTA-6628.

Various *Pisum sativum* lines of this invention can be used to transmit the slow-maturing, determinate pea trait to new varieties using various cross pollination and selection methods. Therefore, breeders may obtain hybrids using the described slow-maturing, determinate pea plants and lines for further selfing and subsequent selection. Using standard crossing techniques, those of skill in the art may also obtain commercial slow-maturing, determinate peas with desirable traits besides those described above. For example, breeders may easily obtain commercial *Pisum sativum* lines with the preferred trait of dark green pea color, disease resistance traits, traits relating to optimized yield under specific growth conditions and other agronomic or consumer preferred characteristics.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

DEPOSIT INFORMATION

A deposit of the Seminis Vegetable Seeds, Inc., proprietary inbred *Pisum sativum* line 085 2 0698, disclosed above and recited in the appended claims has been made with the American Type Culture Collection, Accession No. PTA-6628. The date of the deposit is Mar. 11, 2005. The deposit of 2500 seeds for this variety were taken from the same deposit maintained by Seminis Vegetable Seeds, Inc., since prior to the filing date of this application.

Upon issuance of a patent, all restrictions upon the deposit will be removed, and the deposit is intended to meet all of the requirements of 37 C.F.R. §1.801-1.809.

What is claimed is:

1. A determinate pea plant having a dark green and wrinkled seed or pea.

2. The pea plant of claim 1 having a genotype pa/pa.

3. The pea plant of claim 1 having a double wrinkled-seed genotype.

4. The pea plant of claim 3, wherein said double wrinkled-seed genotype is r/r, rb/rb.

5. A plurality of the pea plant of claim 1 grown in a field.

6. Pods of the pea plant of claim 1.

7. Immature peas of the pea plant of claim 1.

8. The pea plant of claim 1, having a genotype det/det.

9. The pea plant of claim 1, having a genotype det r/det r.

10. The pea plant of claim 1, having genotype det r/det r, rb/rb.

11. The pea plant of claim 1, having a genotype pa det r/pa det r, rb/rb.

12. A method of producing a pea crop comprising growing a plurality of pea plants of claim 1 and harvesting peas from said pea plants.

13. The method of claim 12, wherein said harvest is by mechanical means.

* * * * *

UNITED STATES PATENT AND TRADEMARK OFFICE
CERTIFICATE OF CORRECTION

PATENT NO. : 8,269,067 B2
APPLICATION NO. : 12/973702
DATED : September 18, 2012
INVENTOR(S) : David Webster et al.

It is certified that error appears in the above-identified patent and that said Letters Patent is hereby corrected as shown below:

Gene names, for example, r, rb, lam, det, pa, rug3, are italicized in the original specification as filed, but are not italicized throughout the Letters Patent.

r needs to be italicized at column 2, lines 1, 4 and 7; column 4, lines 10 and 11; column 6, lines 6, 8, 32, and 36; column 7, lines 34, 35 and 65; column 9, line 38; column 10, line 43; column 12, lines 21 and 29; column 16, lines 24 and 31;

rugosus needs to be italicized at column 1, line 47;

rb needs to be italicized at column 1, lines 60, 64 and 66; column 2, lines 1, 4 and 7; column 4, line 48; column 6, lines 1, 8 (twice), and 32; column 7, lines 34, 35 and 64; column 8, line 2; column 9, lines 26, 37 (twice), 39, and 56 (twice); column 12, lines 22 and 31;

alsweet needs to be italicized at column 1, line 66;

rug3 needs to be italicized at column 2, lines 7 and 9; column 7, lines 43 and 40;

rug4 needs to be italicized at column 2, lines 7 and 10; column 7, line 53;

rug5 needs to be italicized at column 2, lines 7 and 10; column 7, line 46;

lam needs to be italicized at column 2, lines 8 and 10; column 7, line 46;

det needs to be italicized at column 2, lines 46, 50 and 53; column 7, lines 17 and 65; column 11, line 56; column 12, lines 5 and 21;

pa needs to be italicized at column 2, lines 50 and 53; column 7, line 65; column 11, line 56; column 12, lines 5 and 21;

in cis needs to be italicized at column 5, lines 63 and 66;

in trans needs to be italicized at column 5, line 63;

Taq needs to be italicized at column 13, line 66.

Additionally, at column 13, line 66, please change "2.54" to read -- 2.5 µL --.

Signed and Sealed this
Twenty-second Day of January, 2013

David J. Kappos
*Director of the United States Patent and Trademark Office*

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial
<220> FEATURE:
<223> OTHER INFORMATION: primer

<400> SEQUENCE: 1
agggcctgga acacatctct atc                                           23

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
caacaattca tatcataaaa ctcactc                                       27

<210> SEQ ID NO 3
<211> LENGTH: 700
<212> TYPE: DNA
<213> ORGANISM: Pisum sativum
<220> FEATURE:
<221> NAME/KEY: CDS
<222> LOCATION: (37)..(219)
<220> FEATURE:
<221> NAME/KEY: CDS
<222> LOCATION: (396)..(521)
<220> FEATURE:
<221> NAME/KEY: CDS
<222> LOCATION: (631)..(699)

<400> SEQUENCE: 3
aactcaaaaa aagcttagtt ttttgaggtt actaca atg gct tct ggt tgt gtg        54
                                        Met Ala Ser Gly Cys Val
                                         1               5 agc ttg aaa acc aac acc cat ttt cca aat tct aaa aaa ggt tct ttt       102
Ser Leu Lys Thr Asn Thr His Phe Pro Asn Ser Lys Lys Gly Ser Phe
         10                  15                  20 ttt ggg gaa aga atc aaa gga agc ttg aaa aac agt tca tgg gtc act       150
Phe Gly Glu Arg Ile Lys Gly Ser Leu Lys Asn Ser Ser Trp Val Thr
             25                  30                  35 acc cag aag aag atc aaa cct gct tct ttt tct gct att ctt act tca       198
Thr Gln Lys Lys Ile Lys Pro Ala Ser Phe Ser Ala Ile Leu Thr Ser
     40                  45                  50 gat gac ccc aaa ggt tcc ctg gtaaactcag tttcattctg ggtttcactt          249
Asp Asp Pro Lys Gly Ser Leu
55                  60 tttgcttcca attctgaaaa aaagaaagac ttttttttc tcccattata tgacataact      309
```

```
tttttatgtt aattattttg ctacattttg tttggtatat gattatgatt atgattatga    369
ttttgagtgt atgttttgaa attcag aat ttg caa gtg cct tca ttt ctg aga    422
                              Asn Leu Gln Val Pro Ser Phe Leu Arg
                                          65                  70 cta aga gct gat cca aaa aat gtg att tcc att gtg ttg gga gga ggg    470
Leu Arg Ala Asp Pro Lys Asn Val Ile Ser Ile Val Leu Gly Gly Gly
             75                  80                  85 cct gga aca cat ctc tat cct ctt acc aaa cga gct gca aca cct gcg    518
Pro Gly Thr His Leu Tyr Pro Leu Thr Lys Arg Ala Ala Thr Pro Ala
         90                  95                 100 gtt gagtgagttt tatgatatga attgttgtct gaattctaac attttggtgt         571
Val tgtttgtaac tttgtgctgt ttgtgatgaa gatttgtttg ctgtgtttgt tttgaaggt    630 cct gtt gga gga tgc tat agg ctt ata gac att cca atg agc aac tgc    678
Pro Val Gly Gly Cys Tyr Arg Leu Ile Asp Ile Pro Met Ser Asn Cys
        105                 110                 115 atc aat agt ggc atc aac aag a                                      700
Ile Asn Ser Gly Ile Asn Lys
120                 125

<210> SEQ ID NO 4
<211> LENGTH: 126
<212> TYPE: PRT
<213> ORGANISM: Pisum sativum

<400> SEQUENCE: 4

Met Ala Ser Gly Cys Val Ser Leu Lys Thr Asn Thr His Phe Pro Asn
1               5                   10                  15

Ser Lys Lys Gly Ser Phe Phe Gly Glu Arg Ile Lys Gly Ser Leu Lys
            20                  25                  30

Asn Ser Ser Trp Val Thr Thr Gln Lys Lys Ile Lys Pro Ala Ser Phe
        35                  40                  45

Ser Ala Ile Leu Thr Ser Asp Asp Pro Lys Gly Ser Leu Asn Leu Gln
    50                  55                  60

Val Pro Ser Phe Leu Arg Leu Arg Ala Asp Pro Lys Asn Val Ile Ser
65                  70                  75                  80

Ile Val Leu Gly Gly Gly Pro Gly Thr His Leu Tyr Pro Leu Thr Lys
                85                  90                  95

Arg Ala Ala Thr Pro Ala Val Pro Val Gly Gly Cys Tyr Arg Leu Ile
            100                 105                 110

Asp Ile Pro Met Ser Asn Cys Ile Asn Ser Gly Ile Asn Lys
        115                 120                 125

<210> SEQ ID NO 5
<211> LENGTH: 691
<212> TYPE: DNA
<213> ORGANISM: Pisum sativum

<400> SEQUENCE: 5
aactcaaaaa aagcttagtt ttttgaggtt actacaatgg cttctggttg tgtgagcttg    60
aaaaccaaca cccattttcc aaattctaaa aaaggttctt ttttggggga agaatcaaa    120 ggaagcttga aaacagttc atgggtcact acccagaaga agatcaaacc tgcttctttt    180
tctgctattc ttacttcaga tgaccccaaa ggttccctgg taaactcagt tcattctgg    240 gtttcacttt ttgcttccaa ttctgaaaaa agaaagact ttttttttct cccattatat    300
gacataactt tttatgtta attattttgc tacattttgt ttggtatatg attatgatta    360
tgattatgat tttgagtgta tgttttgaaa ttcagaattt gcaagtgcct tcatttctga    420
```

```
gactaagagc tgatccaaaa aatgtgattt ccattgtgtt gggaggaggg cctggaacac    480
atctctatcc tcttaccaaa cgagctgcgg ttgagtgagt tttatgatat gaattgttgt    540
ctgaattcta acattttggt gttgtttgta actttgtgct gtttgtgatg aagatttgtt    600
tgctgtgttt gttttgaagg tcctgttgga ggatgctata ggcttataga cattccaatg    660
agcaactgca tcaatagtgg catcaacaag a                                   691
```